(12) United States Patent
Nagl

(10) Patent No.: US 8,652,435 B2
(45) Date of Patent: Feb. 18, 2014

(54) HIGH PRESSURE REDUCTION-OXIDATION DESULFURIZATION PROCESS

(71) Applicant: Merichem Company, Houston, TX (US)

(72) Inventor: Gary J. Nagl, Deer Park, IL (US)

(73) Assignee: Merichem Company, Houston, TX (US)

( * ) Notice: Subject to any disclaimer, the term of this patent is extended or adjusted under 35 U.S.C. 154(b) by 0 days.

(21) Appl. No.: 13/736,314

(22) Filed: Jan. 8, 2013

(65) Prior Publication Data

US 2013/0123561 A1    May 16, 2013

Related U.S. Application Data

(63) Continuation of application No. 12/913,448, filed on Oct. 27, 2010, now Pat. No. 8,372,365.

(51) Int. Cl.
| | | |
|---|---|---|
| *B01D 53/52* | (2006.01) | |
| *B01D 53/78* | (2006.01) | |
| *B01D 53/86* | (2006.01) | |
| *B01D 53/96* | (2006.01) | |
| *C07C 7/152* | (2006.01) | |
| *C01B 17/05* | (2006.01) | |

(52) U.S. Cl.
USPC ........ 423/576.6; 423/220; 423/225; 423/226; 423/231; 423/573.1; 423/576.4; 423/576.5; 423/576.7; 585/850

(58) Field of Classification Search
USPC .............. 423/220, 225, 226, 230, 231, 573.1, 423/576.4, 576.5, 576.6, 576.7; 585/850
See application file for complete search history.

(56) References Cited

U.S. PATENT DOCUMENTS

| | | |
|---|---|---|
| 4,622,212 A | 11/1986 | McManus et al. |
| 4,808,385 A | 2/1989 | Grinstead |

*Primary Examiner* — Stuart Hendrickson
*Assistant Examiner* — Daniel Berns
(74) *Attorney, Agent, or Firm* — McDonnell Boehnen Hulbert & Berghoff LLP

(57) ABSTRACT

An improved process for reduction-oxidation desulphurization uses an oxidizer operating at a pressure greater than the absorber where a liquid reduction-oxidation catalyst solution contacts a sulfur-containing gas feed stream.

6 Claims, 1 Drawing Sheet

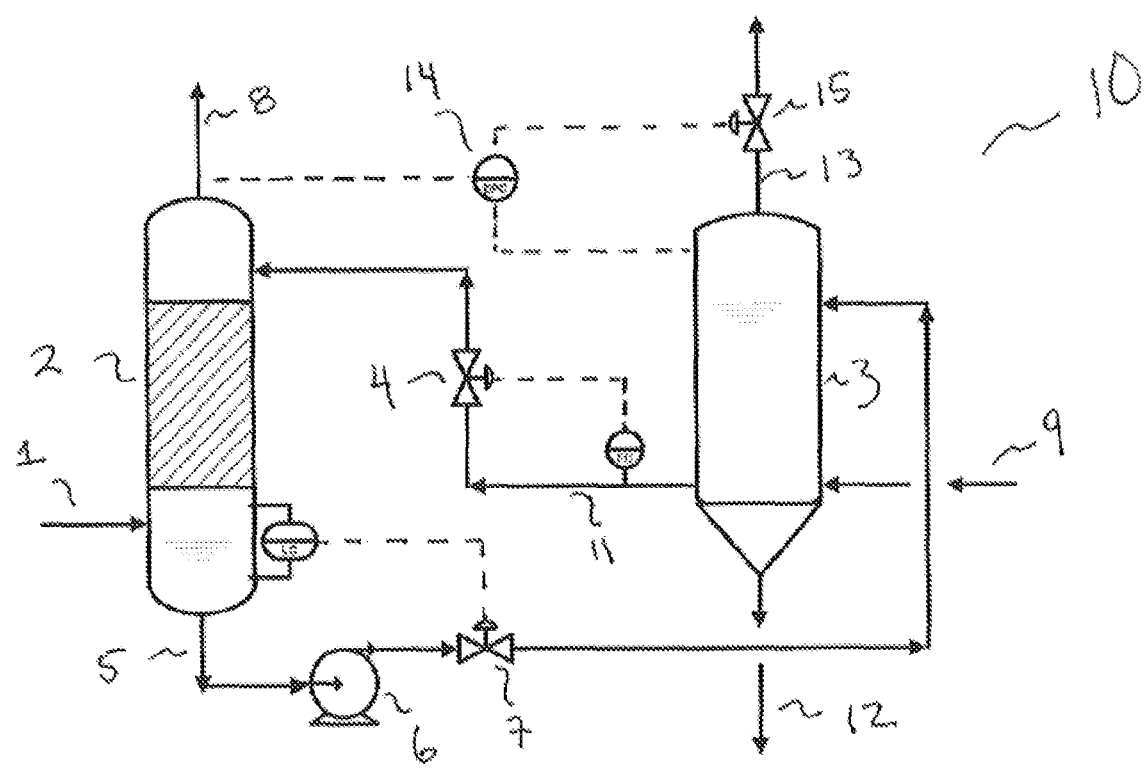

HIGH PRESSURE REDUCTION-OXIDATION DESULFURIZATION PROCESS

FIELD OF THE INVENTION

This invention relates to an improved reduction-oxidation (Redox) process for treatment of sour gas streams containing hydrogen sulfide. Specifically, a high-pressure oxidizer is used in combination with a high-pressure absorber.

BACKGROUND

Hydrogen sulfide is a major source of pollution of gas streams since it is liberated as a waste by-product in a number of chemical processes, such as sulfate or kraft paper pulp manufacture, viscose manufacture, sewage treatment, the production of organic sulfur compounds, as well as during petroleum refining and in the production of natural gas and combustible gases from coal, such as in coking operations. Hydrogen sulfide is also present in geothermal steam, which is captured for use in power generating plants.

To eliminate these polluting sulfur gases the art has developed several oxidation-reduction ("redox") processes that use an aqueous chelated metal catalyst solution for removing hydrogen sulfide from a gas stream. In those prior art processes a hydrogen sulfide-containing gas, known as "sour gas," is contacted with a chelated metal catalyst to effect absorption. Subsequent oxidation of the hydrogen sulfide to elemental sulfur and concurrent reduction of the metal to a lower oxidation state also occurs. The catalyst solution is then regenerated for reuse by contacting it with an oxygen-containing gas to oxidize the metal back to a higher oxidation state. The elemental sulfur is continuously removed from the process as a solid product with high purity. Illustrative, but not exclusive, of these oxidation-reduction processes is the description contained in U.S. Pat. No. 4,622,212 and the references cited therein.

In order to return the "spent" liquid redox catalyst solution to its original oxidation level so it can be recycled for subsequent use in the process, oxygen must be supplied to the spent redox catalyst solution. This is typically accomplished using an oxidation process where various mechanical apparatus, including well-known tank spargers, use compressed air as the source of oxygen. Typically, such oxidation processes are operated at pressures lower than the pressure of the reduction portion of the process, i.e., the absorber, more typically at about atmospheric pressure. Use of low pressure oxidizers are a result of an attempt to minimize capital costs by eliminating the need for more expensive high pressure equipment. Although initial capital cost of equipment may be lower, operating at a large pressure differential between the absorber and the oxidizer has a host of other inherent problems. For example, in these previously known processes, the higher pressure redox solution exiting the absorber must be reduced in pressure before entering the oxidizer. This is typically accomplished through a flash drum or a series of flash drums. Reducing pressure of the redox solution has unfortunate consequences, such as foaming, lost of gas product, and rapid erosion of control valves due to the suspended solid sulfur particles. All of these problems reduce the overall process economics and the operability of the process.

Up until now, the art has failed to come up with a high pressure reduction oxidation process that eliminates the above problems, yet still provides a cost effective process for the removal of sulfur from hydrocarbon process streams.

These and other advantages will become evident from the following more detailed description of the invention.

SUMMARY

This invention relates to an improved reduction oxidization process for use in treating hydrogen sulfide containing gas streams. The improved process operates the oxidizer section of the process at a higher operating pressure than the reduction section, i.e., the absorber. This higher pressure differential eliminates the need for pressure reducing equipment, such as a flash drum. The design of the oxidizer is not critical to our process, likewise the design of the absorber is not critical, provided that both unit operations can operate at internal pressures greater than 100 psig and temperatures of approximately 125° F. Although any oxygen containing gas can be used in this invention, the most commonly known and most available, air, will be referred to below for the sake of brevity.

Pressurized air introduced to the interior of the oxidizer maintains the operating pressure higher than the operating pressure of the absorber, which operates at pressures greater than 100 psig. Preferably, the oxidizer is controlled to operate at pressures about 5 to about 10 psi higher than the operating pressure of the absorber to minimize compression costs. The higher pressure in the oxidizer is preferably maintained using high pressure air as the oxidizing gas to regenerate the metal catalyst solution, as explained below. Operating the oxidizer at pressures exceeding atmospheric results in a higher oxygen partial pressure within the oxidizer, and since the amount of oxygen required to reoxidize the catalyst is inversely proportional to the oxygen partial pressure less air is required as the oxidizer pressure is increased.

The high pressure absorber and oxidizer combination of my invention is preferably used in processes to treat hydrocarbon gas streams to convert $H_2S$ to elemental sulfur utilizing an aqueous redox solution containing a chelated iron catalyst. The $H_2S$ containing gas stream (sour gas) is contacted with the aqueous redox solution where the $H_2S$ is absorbed and converted to elemental sulfur and where a portion of the iron is reduced from the ferric state ($Fe^{+++}$) to the ferrous state ($Fe^{++}$). All or a portion of the redox solution containing the ferrous state iron is then introduced into an oxidizer where compressed air is introduced to the redox solution where it preferably contacts the redox solution as very tiny bubbles having a high surface area. This causes the ferrous iron to regenerate back (oxidize) to the ferric state (regeneration step). Regenerated metal chelate catalyst solution is then returned (recycled) to the process to be used again to catalyze the oxidation of the $H_2S$. Sulfur is removed from the system by passing a portion or all of the solution from the oxidizer through a sulfur recovery device, where the sulfur is removed from the process. Because the oxidizer in my invention is operating at a pressure greater than 100 psig the sulfur recovery device must be capable of separating solid elemental sulfur at greater than atmospheric pressure and reducing the pressure to atmospheric at the sulfur outlet of the device. Such a sulfur recovery device is referred to in the art as a "lock hopper" system.

Although a number of polyvalent metals can be used to formulate the metal chelate catalyst used in the process of this invention, a preferred polyvalent metal is iron. The series of reactions involved in catalytically oxidizing hydrogen sulfide to elemental sulfur using an iron chelate catalyst can be represented by the following reactions, where L represents the particular ligand chosen to formulate the metal chelate catalyst:

$$H_2S_{(gas)} + H_2O_{(liq.)} \rightarrow H_2S_{(aqueous)} + H_2O_{(liq.)} \qquad (1)$$

$$H_2S_{(aqueous)} \rightarrow H^+ + HS^- \quad (2)$$

$$HS^- + 2(Fe^{3+}L_2) \rightarrow S_{(solid)} + 2(Fe^{2+}L_2) + H^+ \quad (3)$$

By combining equations (1) through (3) the resulting equation is:

$$H_2S_{(gas)} + 2(Fe^{3+}L_2) \rightarrow 2H^+ + 2(Fe^{2+}L_2) + S_{(solid)} \quad (4)$$

In order to have an economical workable process for removing hydrogen sulfide from a gaseous stream when a ferric iron chelate is used to effect catalytic oxidation of the hydrogen sulfide, it is essential that the ferrous iron chelate formed in the above described manner be continuously regenerated by oxidizing to ferric iron chelate on contacting the reaction solution with dissolved oxygen, preferably obtained from introduction of high pressure ambient air, in the same or in a separate contact zone. The series of reactions which take place in the oxidizer of our invention when regenerating the metal chelate catalyst can be represented by the following equations:

$$O_{2(gas)} + 2H_2O \rightarrow O_{2(aqueous)} + 2H_2O \quad (5)$$

$$O_{2(aqueous)} + 2H_2O + 4(Fe^{2+}L_2) \rightarrow 4(OH^-) + 4(Fe^{3+}L_2) \quad (6)$$

By combining equations (5) through (6), the resulting equation (7) is:

$$\tfrac{1}{2}O_2 + H_2O + 2(Fe^{2+}L_2) \rightarrow 2(OH^-) + 2(Fe^{3+}L_2) \quad (7)$$

And, when equations (4) and (7) are combined, the overall process can be represented by the following equation:

$$H_2S_{(gas)} + \tfrac{1}{2}O_{2(gas)} \rightarrow S_{(solid)} + H_2O_{(liq.)} \quad (8)$$

It has been found that not all iron chelating agents capable of forming a complex in aqueous solutions with iron in the ferric valence state ($Fe^{3+}$) or in the ferrous valence state ($Fe^{2+}$) are suitable for use over the broad range of operating conditions employed for this oxidation-reduction system for the removal of hydrogen sulfide. Among the iron chelate reagents which have been used in prior art processes for removing hydrogen sulfide are the aminopolycarboxylic acid-type chelating agents, such as ethylenediamine tetraacetic acid and the alkali metal salts thereof.

As mentioned, one object of this invention is to eliminate the problems associated with a conventional redox process, such as foaming and loss of product gas in the flash drum(s) where the absorber is operated at high pressure and the oxidizer is operated at roughly atmospheric pressure. In the invention described herein any product gas, which is dissolved in the solution leaving the high pressure absorber, will remain in solution until it reenters the high pressure absorber where a small amount of product gas will flash out of solution and enter the product gas stream.

The above-stated object is accomplished by providing an oxidizer that operates at a higher pressure than the absorber, preferably from about 5 to about 10 psi higher in pressure than the absorber. The absorber preferably is operated at greater than 100 psig.

Another embodiment of our invention involves providing a system for oxidizing a liquid reduction-oxidation catalyst solution comprising a source of pressurized air; an oxidizer vessel capable of maintaining an operating pressure of P2, where P2≥P1+5 psi and P1 is the pressure of the absorber and is greater than 100 psig. The pressurized air is fed to the oxidizer to regenerate the metal catalyst solution and to maintain the pressure differential between the absorber and the oxidizer.

Yet another embodiment of our invention relates to a process for continuously removing hydrogen sulfide from a gas where the gas feed is directed to the oxidation-reduction process where it is contacted with a chelated metal catalyst in an absorber operating at a pressure greater than 100 psig to produce a first stream of hydrogen sulfide-free product gas and a second stream comprising elemental sulfur and chelated metal catalyst solution; removing the first stream from the process; providing a high pressure oxidizer vessel operating at a pressure greater than the absorber; directing at least a portion of the second stream to the oxidizer along with a pressurized air stream to contact the second stream; and separating elemental sulfur from the chelated metal catalyst solution.

These and other objects will become more apparent from the detail description of the preferred embodiment contained below.

BRIEF DESCRIPTION OF THE FIGURES

FIG. 1 schematically illustrates one possible embodiment of the redox process of my invention.

DETAILED DESCRIPTION

As stated, our invention concerns a novel high pressure oxidizer that can be used to regenerate a liquid redox catalyst solution. This oxidizer can be used to provide a new process flow scheme for the desulphurization of a sour gas. Operating temperatures for the oxidizer can range from about 25° C. to about 55° C. Operating pressures are preferably greater than 100 psig and more preferably greater than 5 psi higher that the absorber operating pressure from which the oxidizer is in fluid communication.

Turning now to the FIGURE that schematically illustrates such a desulfurization process 10 for treatment of gas streams contaminated with $H_2S$. As shown, a waste gas stream (sour gas) is delivered via feed line 1 to an absorber 2 where it is contacted with an aqueous chelated iron catalyst solution. Absorber 2 is operated at a pressure greater than 100 psig. The catalyst solution is obtained from high pressure oxidizer 3 via fluid control valve 4. After contacting the feed gas with the liquid redox solution in absorber 2, the spent liquid catalyst solution is removed via line 5 and supplied via pump 6 through liquid level control valve 7 to the inlet of oxidizer 3 operating at a pressure 5 to 10 psi higher than the pressure in absorber 2. The absorber 2 may be of any suitable design to meet the required amount of $H_2S$ removal, i.e. liquid full absorbers, static mixers, packed columns, venturis or mobile bed absorbers. A gas stream, substantially free of $H_2S$, leaves the absorber 2 via line 8. An $O_2$ containing gas stream, preferably high pressure air, is introduced into oxidizer 3 via line 9. The oxidized liquid redox solution is removed from oxidizer 3 through line 11 and introduced into absorber 2. The elemental sulfur is continuously removed from the process by sending a portion of the liquid solution from oxidizer 3 via stream 12, to a lock hopper sulfur recovery device (not shown). The oxidizer 3 pressure is maintained by the combination of high pressure air injection and the differential pressure controller 14 monitoring the absorber pressure and operating pressure control valve 15 on vent line 13.

The invention thus far has been described with particular emphasis on the use of iron as the polyvalent metal of choice; however, other polyvalent metals that form chelates with the ligands described above can also be used. Such additional polyvalent metals include copper, cobalt, vanadium, manganese, platinum, tungsten, nickel, mercury, tin and lead. The chelating agents are generally of the aminopolycarboxylic acid family such as EDTA, HEDTA, MGDA and NTA, or others any one of which can be used in connection with this invention.

In all liquid oxidation-reduction systems, some form of alkaline material must be added to the system to control the pH of the solution. Without the addition of the alkaline material, the pH of the solution will slowly decrease until absorption of $H_2S$ into the solution is no longer great enough to meet the required $H_2S$ removal efficiencies. This decrease in pH is due to the acidic nature of $H_2S$. In addition, if the gas stream being processed contains other acidic species such as carbon dioxide, the pH will decrease even more quickly than with just $H_2S$. Consequently, alkaline materials such as NaOH, KOH, ammonia, alkali metal carbonates, or bicarbonates are generally added to the system to neutralize the acidic components. These materials are generally added to the bulk solution contained in the oxidizer; however, they can be added anywhere in the process.

The foregoing description of the specific embodiments will so fully reveal the general nature of the invention that others can, by applying current knowledge, readily modify and/or adapt for various application such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

The means, materials, and steps for carrying out various disclosed functions may take a variety of alternative forms without departing from the invention. Thus, the expressions "means to . . . " and "means for . . . ", or any method step language as may be found in the specification above or the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation within the terms of the following claims.

The invention claimed is:

1. A desulfurization process comprising the following steps in combination:
   a. continuously feeding a stream of sour hydrocarbon gas containing hydrogen sulfide to an absorber operating at a pressure P1, where P1 is >100 psig;
   b. contacting the sour gas with an aqueous catalyst solution within the absorber to convert the hydrogen sulfide to elemental solid sulfur and generating a spent catalyst solution containing the solid sulfur;
   c. removing a gas stream from the absorber;
   d. pumping the spent catalyst solution containing the solid sulfur into an oxidizer operating a pressure P2, where P2>P1+5 psi;
   e. controlling the pressure of the oxidizer by monitoring the absorber pressure and controlling a valve on the oxidizer vent line;
   f. oxidizing the spent catalyst solution using pressurized air within the oxidizer to form a regenerated catalyst solution;
   g. separating and removing the solid sulfur from the regenerated catalyst solution from the oxidizer; and
   h. removing the regenerated catalyst solution from the oxidizer.

2. The process of claim 1 where the pressurized air is fed to the oxidizer at a pressure P3, where P3>P2.

3. The process of claim 1 where the pressurized air is used to maintain the pressure differential between the oxidizer and the absorber.

4. The process of claim 1 further comprising the absence of a flash drum in fluid communication with the absorber and the oxidizer.

5. The process of claim 1 where the aqueous catalyst solution in the absorber comprises the regenerated catalyst solution removed from the oxidizer.

6. The process of claim 1 where the aqueous catalyst solution comprises a chelated iron catalyst.

* * * * *